(12) United States Patent
Liu

(10) Patent No.: US 11,490,887 B2
(45) Date of Patent: Nov. 8, 2022

(54) SUTURING APPARATUS USING AUTOTRANSFER AND METHOD THEREOF

(71) Applicant: Children's Medical Center Corporation, Boston, MA (US)

(72) Inventor: Kaifeng Liu, Boston, MA (US)

(73) Assignee: Children's Medical Center Corporation, Boston, MA (US)

( * ) Notice: Subject to any disclaimer, the term of this patent is extended or adjusted under 35 U.S.C. 154(b) by 0 days.

(21) Appl. No.: 16/465,875

(22) PCT Filed: Nov. 29, 2017

(86) PCT No.: PCT/US2017/063730
§ 371 (c)(1),
(2) Date: May 31, 2019

(87) PCT Pub. No.: WO2018/102424
PCT Pub. Date: Jun. 7, 2018

(65) Prior Publication Data
US 2020/0360017 A1    Nov. 19, 2020

Related U.S. Application Data

(60) Provisional application No. 62/429,125, filed on Dec. 2, 2016.

(51) Int. Cl.
*A61B 17/06*    (2006.01)
*A61B 17/04*    (2006.01)
*A61B 17/00*    (2006.01)

(52) U.S. Cl.
CPC .... *A61B 17/06066* (2013.01); *A61B 17/0485* (2013.01); *A61B 17/06004* (2013.01); *A61B 17/06166* (2013.01); *A61B 2017/00876* (2013.01); *A61B 2017/0608* (2013.01); *A61B 2017/06042* (2013.01); *A61B 2017/06171* (2013.01)

(58) Field of Classification Search
CPC ............ A61B 17/0469; A61B 17/0485; A61B 17/06066; A61B 17/06061; A61B 17/06004; A61B 17/06166
See application file for complete search history.

(56) References Cited

U.S. PATENT DOCUMENTS

| | | | |
|---|---|---|---|
| 5,431,670 A | 7/1995 | Holmes | |
| 6,719,765 B2 | 4/2004 | Bonutti | |
| 2003/0105474 A1* | 6/2003 | Bonutti | .............. A61B 17/0401 606/139 |

(Continued)

FOREIGN PATENT DOCUMENTS

| | | |
|---|---|---|
| JP | 2006-025932 A | 2/2006 |
| KR | 10-1410572 | 6/2014 |

*Primary Examiner* — Tuan V Nguyen
(74) *Attorney, Agent, or Firm* — Mintz Levin Cohn Ferris Glovsky and Popeo, P.C.; Serge R. Banini

(57) ABSTRACT

A suturing apparatus and method thereof using autotransfer are provided. The suturing apparatus includes a tube that has a rod movable there within and a needle that has an insertion portion. A suture engages with a tip of the needle or the tube. The insertion portion of the needle is inserted through a material prior to engagement with the suture and is withdrawn with the suture back through the material. The suturing system allows for single hand operation, thus simplifying a suturing process.

19 Claims, 15 Drawing Sheets

(56) References Cited

U.S. PATENT DOCUMENTS

2009/0177031 A1* 7/2009 Surti ............... A61B 1/00087
600/106
2015/0100071 A1 4/2015 Phillips et al.

* cited by examiner

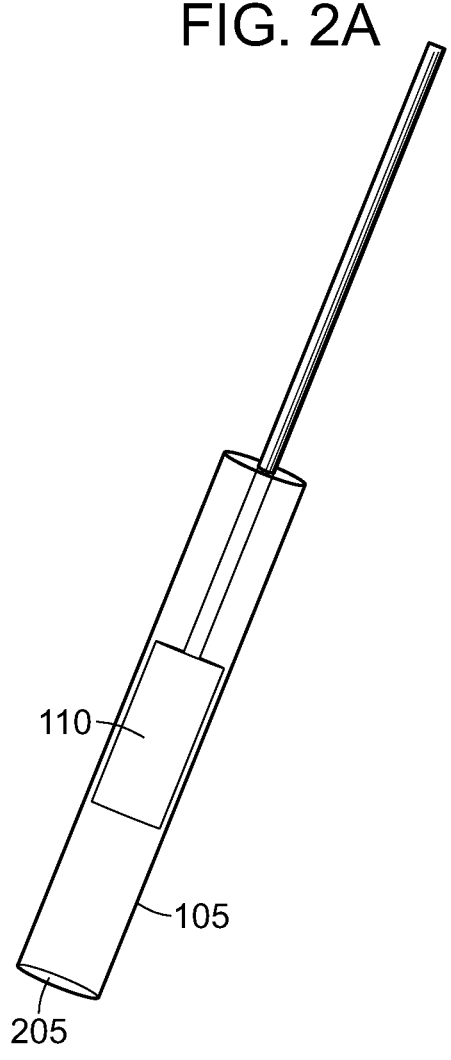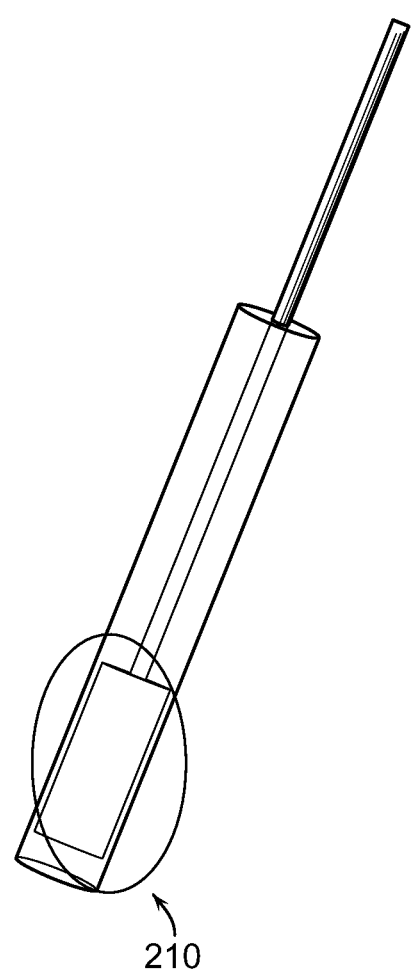

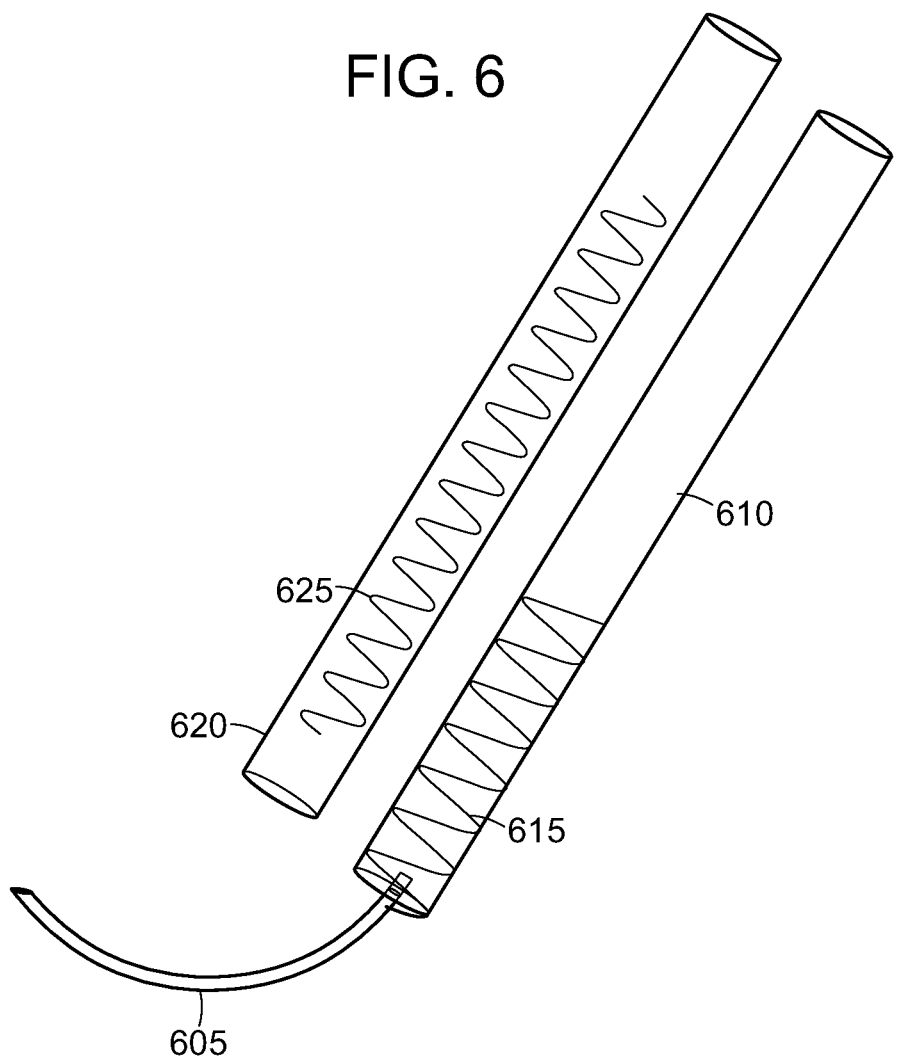

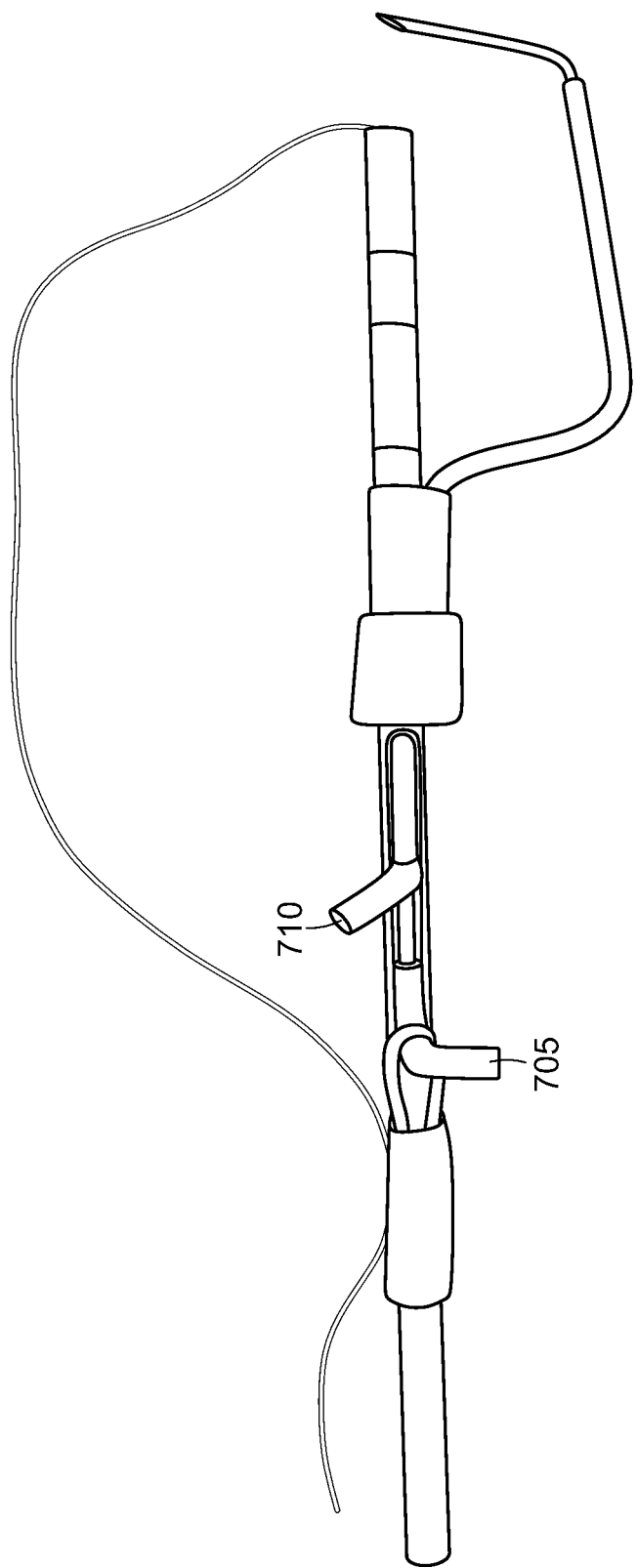

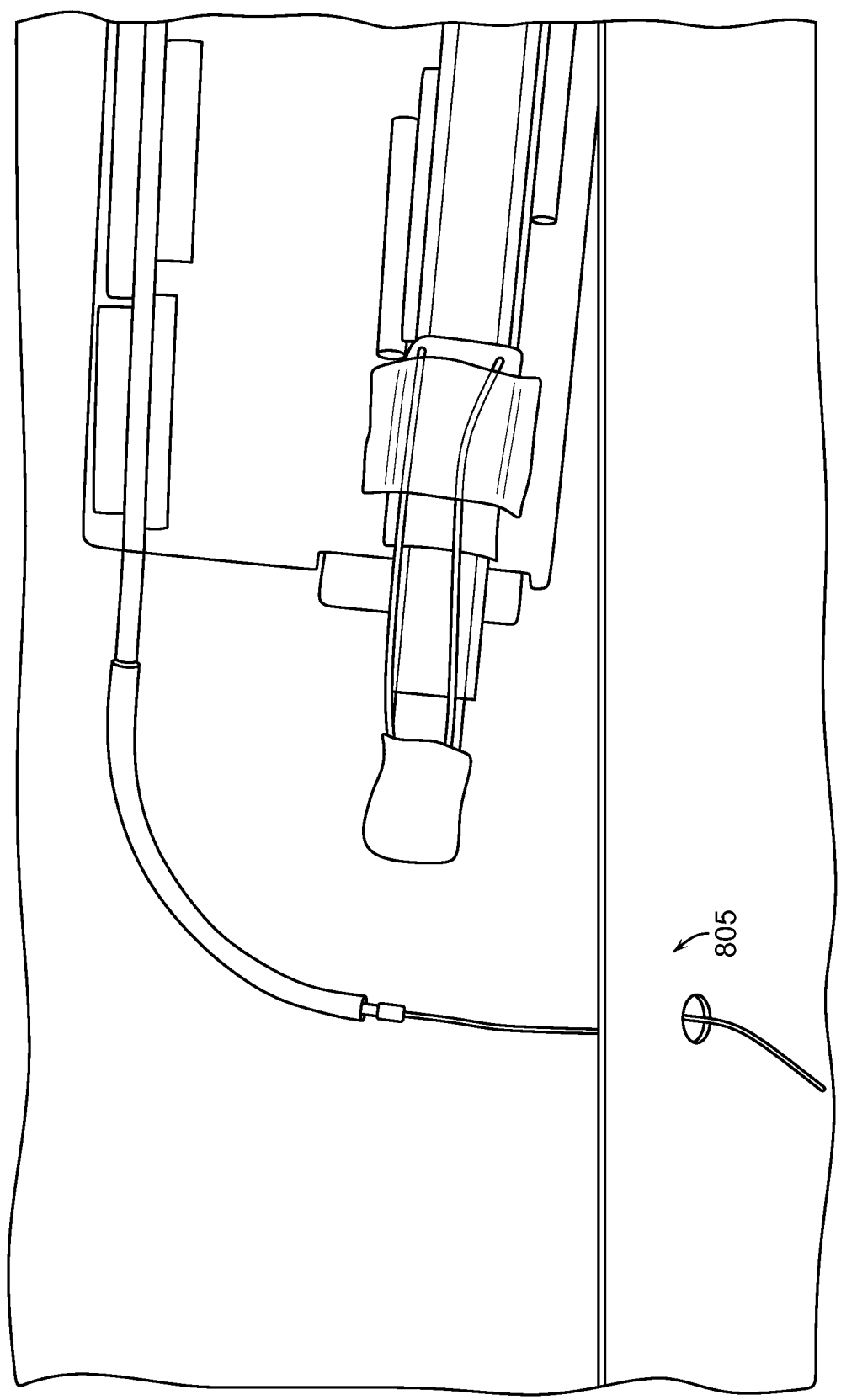

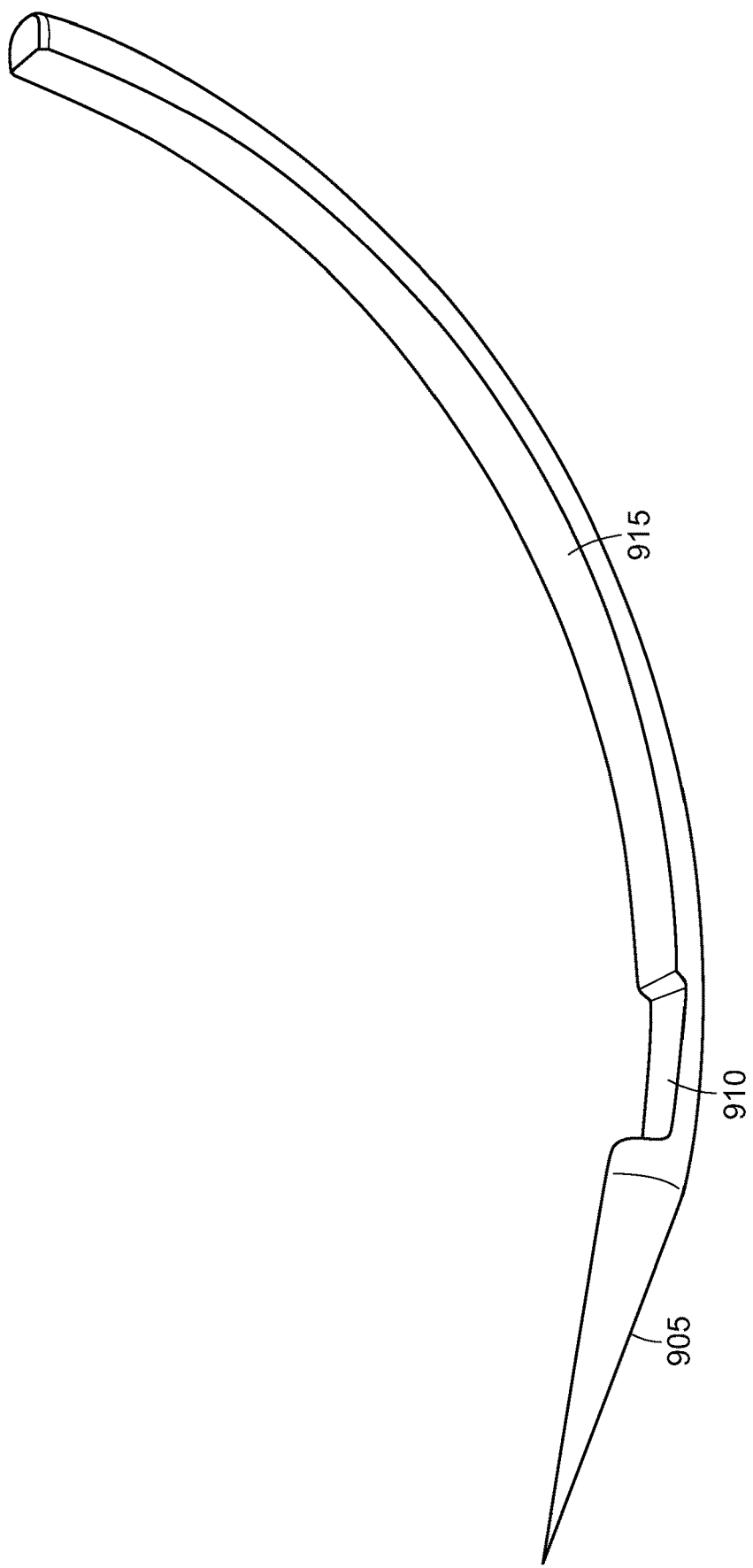

SUTURING APPARATUS USING AUTOTRANSFER AND METHOD THEREOF

RELATED APPLICATIONS

The present application is the National Stage of International Application No. PCT/US2017/063730 filed Nov. 29, 2017, which claims the benefit of U.S. Provisional Application 62/429,125 filed Dec. 2, 2016, which is incorporated herein by reference in their entirety.

BACKGROUND

1. Technical Field

The present disclosure relates generally to a suturing apparatus using autotransfer and a method thereof, and more particularly, to a suturing apparatus in which a suture thread is automatically passed between a needle and a transfer tube to simplify the suturing process.

2. Description of the Related Art

In general, stitches or suturing, in a medical field, are used to bind pieces of material together. Specifically, suturing is used to stitch together pieces of tissue during a surgical procedure. The pieces of tissue will then fuse together during a healing process. A suture needle is typically used to force a suture thread through the layers of tissue to allow the thread to bind the tissue layers.

A typical suture needle includes a needle tip at one end and a suture connection point at the other end. The length of the suture needles also depends on the type of procedure being performed. For example, a longer suture needle is used for large wounds while a short suture needle is used when access or room for manipulation is limited, such as in small and deep spaces. The tip of the needle is inserted through a material by applying insertion force to the suture needle. Additional force is then used to guide the remainder of the suture needle through the material until the entire needle is passed there through. Since the suture thread is coupled to the suture connection point, the thread is pulled along when the insertion force is applied to the suture needle. The process of inserting the needle with suture thread through the material (e.g., tissue) may then be repeated with another layer of material to bind the materials together. This suturing or stitching process, however, also requires the use of a pair of tweezers to grip a portion of the suture needle and pull it through the material. Additionally, due to the size constraints on such traditional suturing needles, accessing certain angle or surgical fields may be difficult.

According to another developed design, a pair of tweezers may include the suture needle between the tips thereof. In particular, a straight double-ended suture needle is moveable between the tips of the tweezers upon engagement of the tweezers. For example, when a user squeezes the tweezer arms together, the suture needle disconnects from one tip and engages with the other tip. The engagement is based on the release of a blade inside the tweezer arm which must capture a groove of the needle and hold the needle within a recess of the arm. When the tweezers are engaged, the other end of the needle enters an opposite recess and another blade must precisely engage with the needle groove to lock the needle in place. This design eliminates the need to push on the needle itself to puncture through a material. However, the design is complex requiring multiple interworking elements within the tweezer arms to lock the needle end in place, thus increasing risk of error use.

SUMMARY

The present disclosure provides a suturing apparatus and method using autotransfer in which a suture thread is automatically transferred between a needle and a transfer tube to simplify the suturing process and decrease the required time for suturing.

According to one aspect of the present disclosure, a suturing system is provided that includes a tube having a rod movable within the tube and a needle having an insertion portion. A suture engages with a tip of the needle or the tube having the rod there within. The insertion portion of the needle is inserted through a material prior to engagement with the suture. In particular, the suture may be magnetically engaged with the tube and the rod or the needle tip. The tip of the needle and the rod within the tube may also be magnetic. The magnetic strength of the rod is greater than that of the needle tip.

Furthermore, when the tube is pushed toward to the needle, the suture is released from the tube and is engaged with the needle tip. Conversely, when the tube and rod are pushed together toward the needle, the suture is released from the needle and engages with the tube having the rod there within. The release and engagement is attributed to the magnetic strength of the tube decreasing as the rod retracts into the tube. In addition, the magnetic strength of the needle tip becomes greater than the magnetic strength at the tube based on the retraction of the rod within the tube.

In an exemplary embodiment, the tube and needle may be mounted to a single interface to thus allow single-hand use of the system. Alternatively, the tube may be disposed within a hollow shaft of the needle. The needle may be curved in such a case so that the tip of the needle is proximate to an end of the tube. The needle may also include a hollow bevel into which the suture is engaged. Additionally, the end of the suture may be magnetic to engage with the tube and rod or the needle tip. The end of the suture may be ring shaped to connect with the tip of the needle upon engagement. The suture engagement may also be based on electromagnetic coils formed within the needle and the tube.

According to another aspect of the present disclosure, a suturing method is provided that includes engaging a suture with a tube and a magnetic rod movable within the tube. A needle is then pierced through a material and the tube is pushed toward the needle to release the suture therefrom and engage the suture with a magnetic tip of the needle. The needle is then withdrawn through the material with the suture. Additionally, the method may include pushing the tube and magnetic rod toward the needle to reengage the suture with the magnetic rod. The magnetic strength of the magnetic rod is stronger than that of the needle tip, thus causing the reengagement with the magnetic rod. The end of the suture may also be magnetic.

According to yet another aspect of the present disclosure, a suturing method is provided that includes engaging a suture with a tube and a rod movable within the tube and piercing a needle through a material. The tube is then pushed toward the needle to release the suture therefrom and engage the suture with a tip of the needle. The needle is withdrawn from the material with the suture. The method may further include pushing the tube and the rod together toward the needle to reengage the suture with the tube and rod. The suture may be magnetically engaged with the tube and rod or the needle and a magnetic strength of the rod is greater than that of the needle.

Notably, the present invention is not limited to the combination of the suturing apparatus element as listed above and may be assembled in any combination of the elements as described herein.

Other aspects of the disclosure are disclosed infra.

BRIEF DESCRIPTION OF THE DRAWINGS

The embodiments herein may be better understood by referring to the following description in conjunction with the accompanying drawings in which like reference numerals indicate identically or functionally similar elements, of which:

FIGS. 2A-2B illustrate the tube and rod components of the suturing system according to an exemplary embodiment of the present disclosure;

FIG. 6 illustrates a suturing system according to yet another exemplary embodiment of the present disclosure;

FIG. 7 illustrates another view of the suturing system of FIG. 5 according to an exemplary embodiment of the present disclosure;

FIG. 8 illustrates the suturing system mounted on an interface according to an exemplary embodiment of the present disclosure;

FIGS. 9A-9E illustrate various formations of a tip of the needle of the suturing system according to an exemplary embodiment of the present disclosure.

Figure 1:
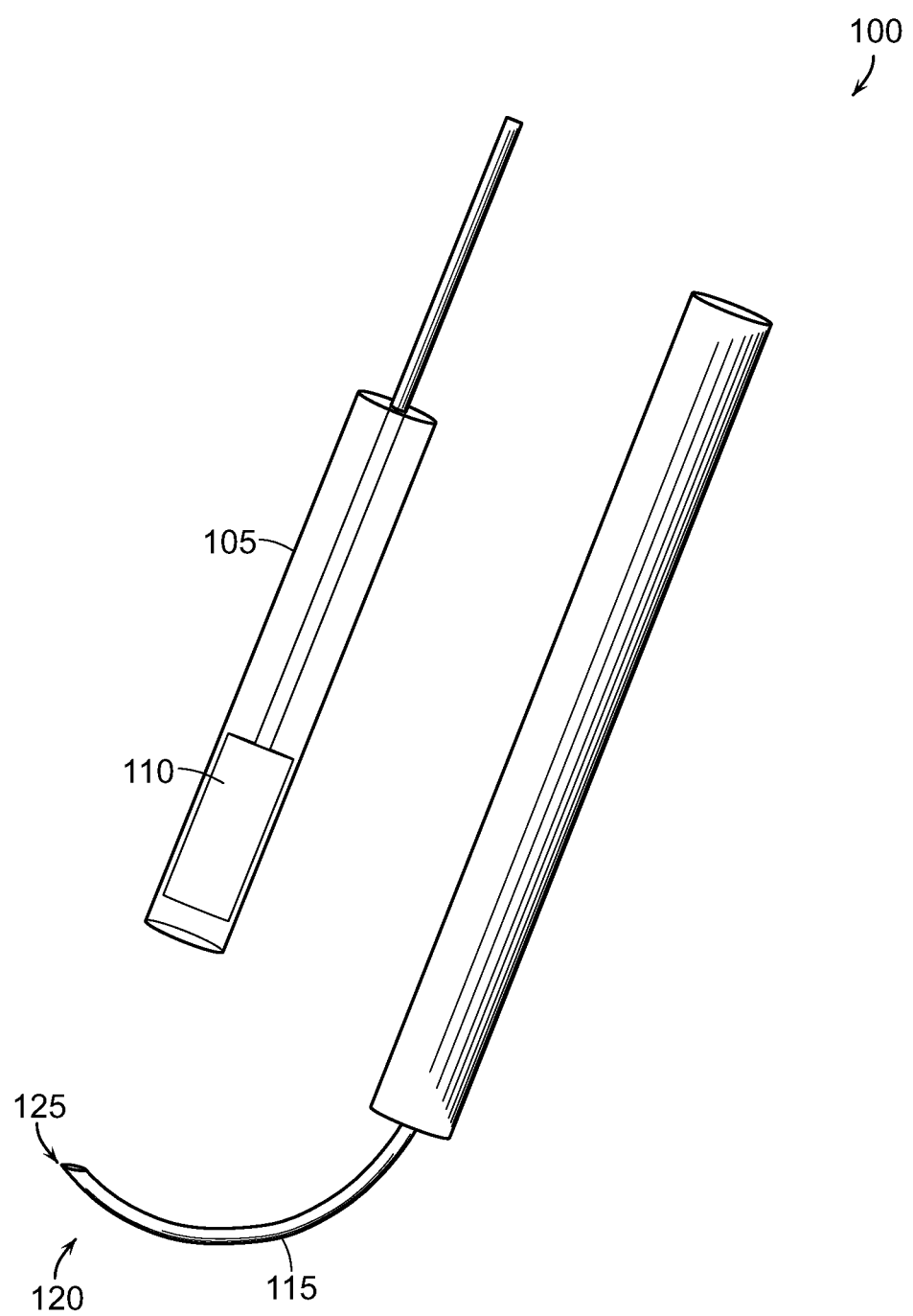
FIG. 1 illustrates a suturing system according to an exemplary embodiment of the present disclosure.

It should be understood that the appended drawings are not necessarily to scale, presenting a somewhat simplified representation of various features illustrative of the basic principles of the disclosure. The specific design features of the present disclosure as disclosed herein, including, for example, specific dimensions, orientations, locations, and shapes will be determined in part by the particular intended application and use environment.

DETAILED DESCRIPTION

The presently disclosed subject matter will be described more fully hereinafter with reference to the accompanying drawings, in which some, but not all embodiments of the inventions are shown. The presently disclosed subject matter may be embodied in many different forms and should not be construed as limited to the embodiments set forth herein; rather these exemplary embodiments are provided so that this disclosure will satisfy applicable legal requirements.

Indeed, many modifications and other exemplary embodiments of the presently disclosed subject matter set forth herein will come to mind to one skilled in the art to which the presently disclosed subject matter pertains, having the benefit of the teachings presented in the foregoing descriptions and the associated drawings. Therefore, it is to be understood that the presently disclosed subject matter is not limited to the specific embodiments disclosed and that modifications and other exemplary embodiments are intended to be included within the scope of the appended claims.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

In one aspect, the present disclosure provides a suturing system that uses autotransfer of a suture thread between a needle and a transfer tube. The suturing system simplifies the suturing process while also decreasing the amount of time required for suturing. Additionally, the system provides for simplified use by allowing the system to be operated single-handedly. A user is not required to physically pull the needle through a material since the suture thread automatically passes between the needle and transfer tube. That is, once the needle tip pierces through the material, the thread is engaged thereto and is pulled through the material. The tube then holds the thread while the needle re-pierces the material. This also allows a user to place stitches in typically inaccessible places.

In surgical applications, the suture may be a suture thread designed for use with organic tissue and may be composed of an absorbable or non-absorbable material. For example, the thread may be composed of an absorbable material such as catgut, polyglycolic acid, polyactic acid, polydioxanone, caprolactone, or the like. Exemplary non-absorbable materials include polypropylene, polyester, nylon, metallic wires, and the like. In some cases, the thread may be coated with a compound that reduces friction during the suturing process, has antibacterial properties, and/or produces a biological reaction in the subject of the procedure (e.g., acts as an anti-inflammatory, etc.).

Referring now to FIG. 1, a suturing system 100 is shown according to an exemplary embodiment of the present disclosure. In particular, the suturing system 100 may include a tube 105 and a needle 115. The tube 105 may specifically have a rod 110 moveable within the tube 105 and the needle 115 may have an insertion portion 120 that is inserted through a material (e.g., living tissue, fabrics, polymers, combinations thereof, and the like having varied thicknesses). The insertion portion may be a hollow bevel into which a suture (e.g., a suture thread) may be engaged. The suture may be selectively engaged with either the tube 105 or the needle 115.

In an exemplary embodiment of the present disclosure, the suture may be magnetically engaged with the tube or the needle. Specifically, the suture may be magnetically engaged with the tube 105 having the rod 110 there within which is magnetic or a tip 125 of the needle 115 which is magnetic as well. The use of magnetic force in this exemplary embodiment allows for the suture to disengage from and engage with one of the needle 115 and the tube 105. Further details regarding the engagement will be described herein below.

Figure 2C:
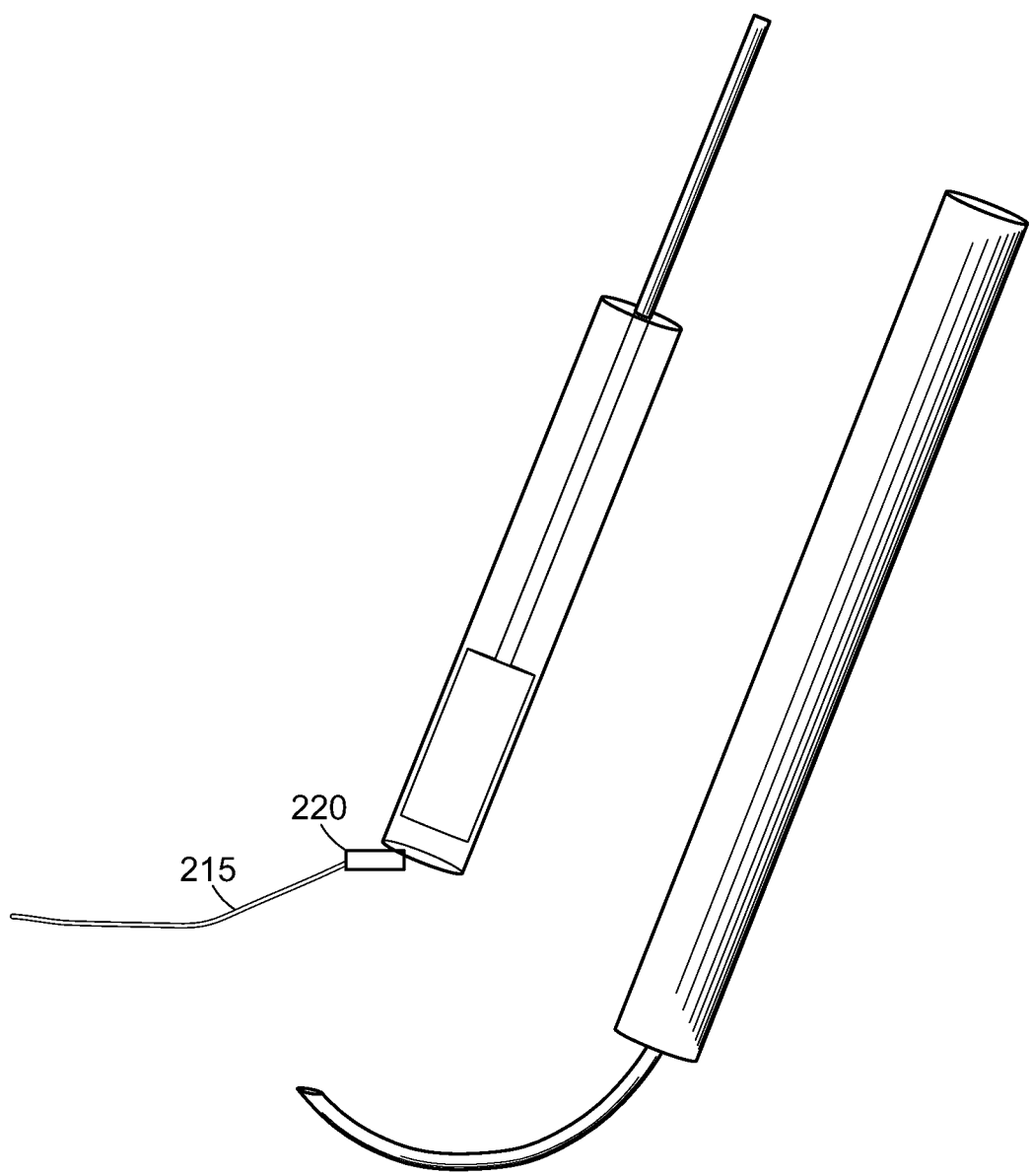
FIG. 2C illustrates a suture engaged with the tube in the suturing system according to an exemplary embodiment of the present disclosure.

FIGS. 2A-2B illustrate the tube 105 (e.g., a transfer tube) and rod 110 components of the suturing system 100 according to an exemplary embodiment of the present disclosure. The rod 110 is movable within the tube 105 and the elements are capable of being moved independent of each other. At least a portion, for example an end, of the rod may be magnetic and thus, as the rod retracts into the tube 105, as shown in FIG. 2A the magnetic force at the opening 205 of the tube 105 decreases. Conversely, as shown in FIG. 2B, when the magnetic portion or end 210 of the rod 110 is pushed toward the tube opening 205, the magnetic strength at the opening of the tube increases (e.g., the magnetic field filtrates from the rod inside the tube). The retraction of the rod 110 into the tube 105 may be caused by the pushing of the tube toward the needle (e.g., an insertion force is applied by the user). In other words, the user is able to either push only the tube toward the needle or alternatively, to increase the magnetic strength that attracts the suture tip toward the opening of the tube, push both the tube and rod together toward the needle. FIG. 2C shows a suture 215 with an end or a tip 220 engaged with the tube 105. Notably, as discussed previously, the suture may be any form of thread (e.g., wire, fiber, etc.) suitable for binding materials together. The end 220 of the suture 215 may be magnetic and thus, may be magnetically engaged with the tube 105 since the rod 110 is disposed at the opening 205 of the tube 105. That is, since the magnetic strength of the rod 110 is greater than the magnetic strength of the needle 115, the suture 215 remains engaged with the tube 105 as shown in FIG. 2C (e.g., a binding force exerted by the rod is greater than the force of the needle tip).

Notably, the engagement with the suture is not limited to the above-described magnetic connection. The suture engagement with the tube or the needle may be through a variety of attractive forces such as mechanical, magnetic, and adhesive techniques that are capable of adjusting the magnetic field strength and direction. As an example, the autotransfer may be accomplished by a technique in which the magnetic field strength and direction at the suture tip changes. That is, the polarity may be reversed such that the suture tip would be attracted and repelled by the magnetic force to attach and detach from the needle tip during suturing. In further detail, the needle and the suture tip may be composed of oppositely polarized magnets or other materials that exhibit magnetic properties when in presence of a magnetic field. Thus, the needle may exert a magnetic force that magnetically couples the suture tip therewith. Then, the suture tip may be released by reversing the polarity of the magnetic field by creating a magnetic force in the opposite direction.

Figure 3B:
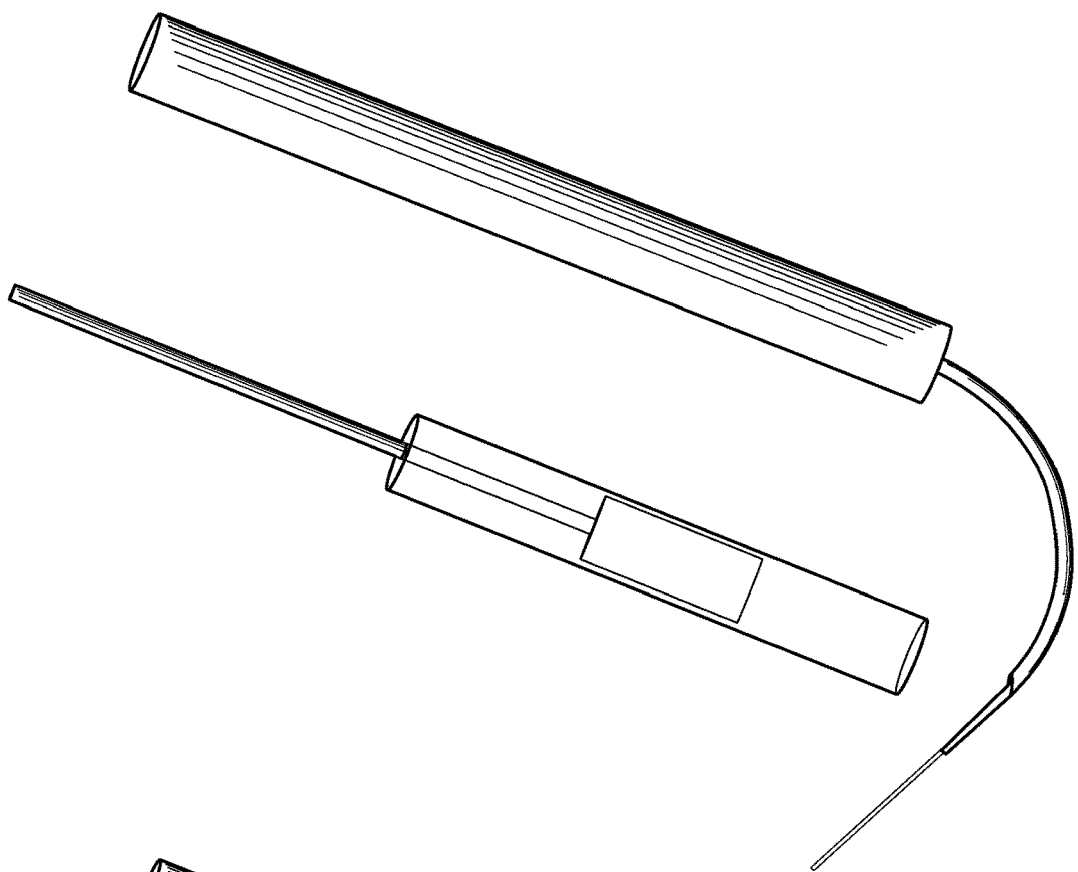
FIGS. 3A-3B illustrate the release of the suture from the tube and rod and engagement of the suture with a needle according to an exemplary embodiment of the present disclosure.
Figure 3A:
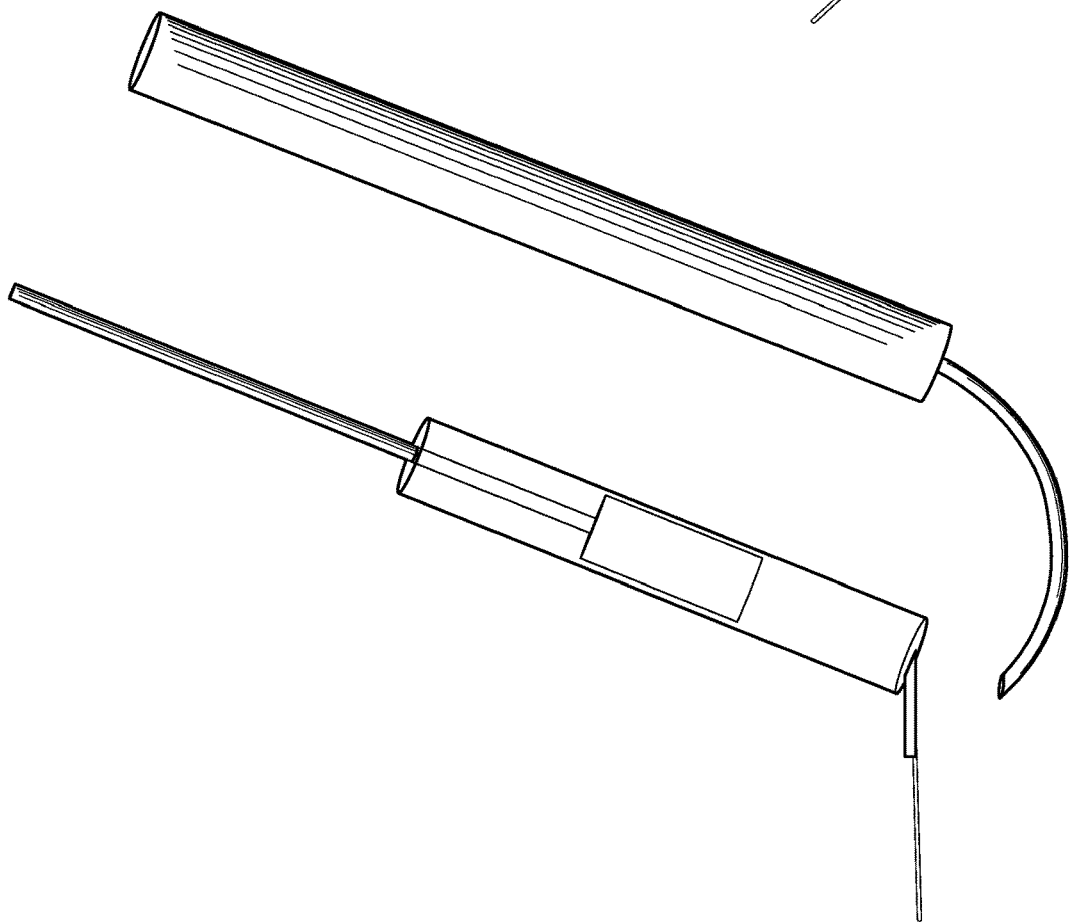

Further, as shown in FIGS. 3A-3B, to disengage or release the end of the suture from the tube 105, the tube 105 is pushed toward the needle 115 which causes the rod 110 to retract within the tube 105. When the rod 110 is retracted into the tube 105, the magnetic strength at the tip of the needle 115 is greater than the magnetic strength at the opening of the tube 105 (e.g., the magnetic field filtrating from the rod within the tube) since the opening of the tube itself is not additionally magnetic. FIG. 3A shows the pushing of the tube 105 toward the needle 115 and FIG. 3B shows the release of the suture from the tube 105 and the engagement of the suture with the needle 115. In other words, the movement of the rod into the tube deactivates the magnetic bond, thus decoupling the suture therefrom. Accordingly, based on the movement, the suture is automatically transferred from one component to the next.

For example, referring to FIGS. 2A-3B, in the initial stage when the suture is engaged with or attached to the tube, the needle may be inserted through a material, such as a tissue. Once the tip of the needle is punctured through the material, the suture may be autotransfered to the tip of the needle based on the pushing of the tube toward the needle. Once the suture is engaged with the needle, the needle may be withdrawn from the material with the suture attached thereto. In other words, the withdrawal of the needle passes the suture thread through the material to begin the suturing process in a medical procedure.

Figure 4B:
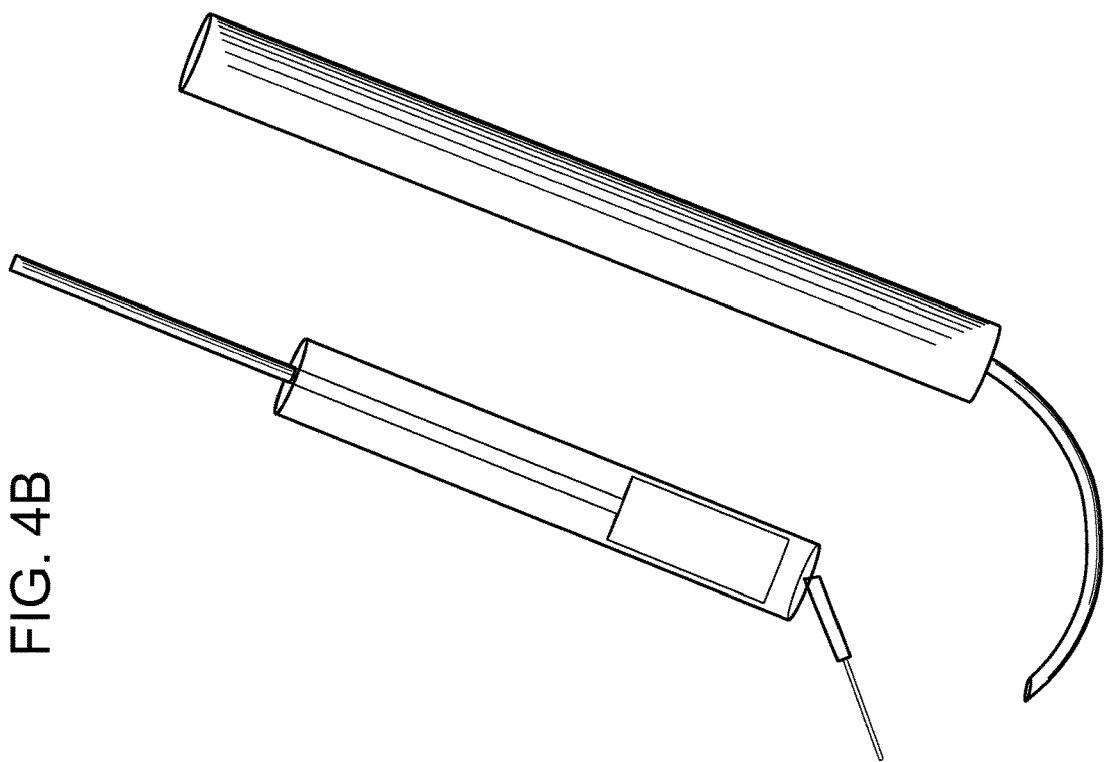
FIG. 4A-4B illustrate the release of the suture from the needle and reengagement of the suture with the tube and rod according to an exemplary embodiment of the present disclosure.
Figure 4A:
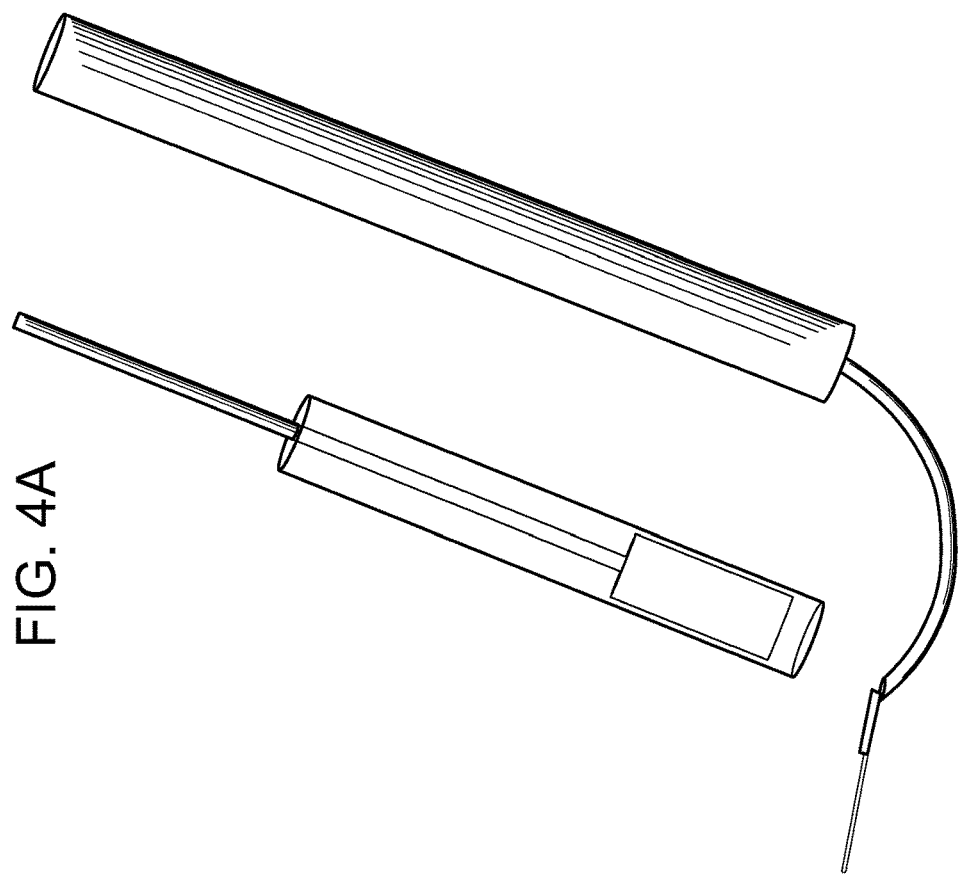

FIGS. 4A-4B illustrate the next step of reengaging the suture with the tube (e.g., by autotransfer). In other words, to continue the suturing process, the suture may be passed back to the tube to allow the needle to once again puncture through the material and then engage the suture thread again to withdraw it through the material (e.g., thus binding the material layers together). Particularly, once the needle 115 has been withdrawn from the material, the tube 105 and the rod 110 may be pushed together toward the needle 115. Thus, since the tube 105 and rod 110 are pushed together toward the needle, the magnetic strength at the opening of the tube 105 is stronger than the magnetic strength of the needle tip 125. Accordingly, the suture releases from the needle tip 125 and reengages with the tube 105. Further, since the suture may be automatically transferred between the needle and the tube after insertion through the material, only the insertion portion of the needle is required to puncture through the tissue. In other words, the system eliminates the need for the entire needle to be passed through the tissue. Once the insertion portion punctures through the material, the suture is autotransfered to the tip of the needle and then the insertion portion may be withdrawn from the material in a reverse direction. Accordingly, the system is capable of preventing inadvertent puncturing of neighboring tissues during a suturing process.

Figure 5:
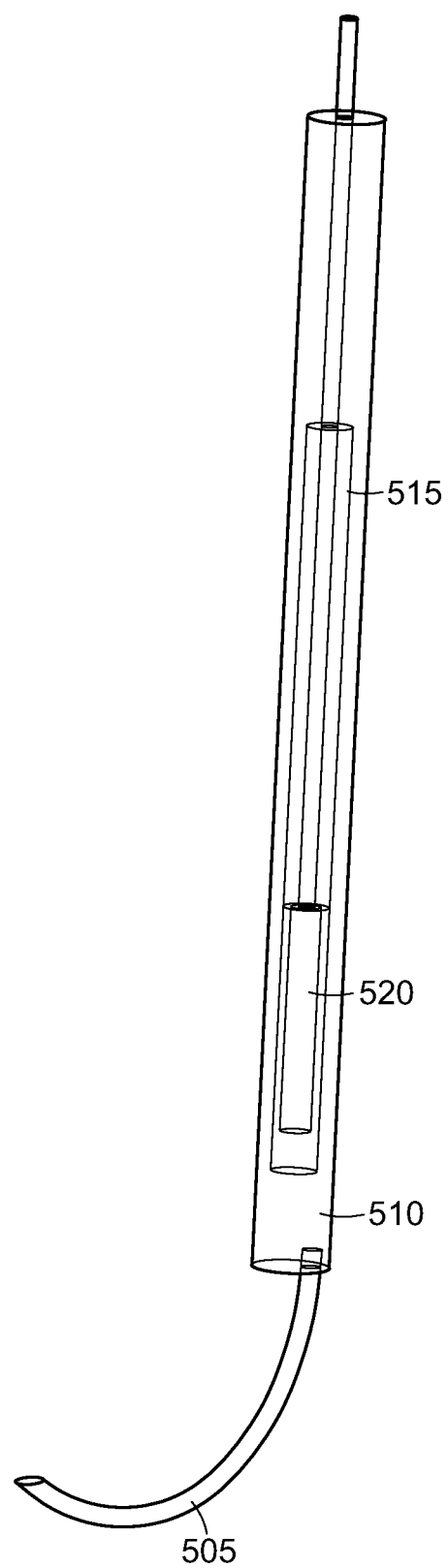
FIG. 5 illustrates a suturing system according to another exemplary embodiment of the present disclosure.

In another exemplary embodiment of the present disclosure, as shown in FIG. 5, a tube 515 and rod 520 may be accommodated within a shaft 510 of a needle 505. The integration of the various components into a single instrument component provides a simplified system that occupies less space in a surgical environment. FIG. 7 shows an exemplary system setup of the system in FIG. 5. As shown, the needle may be curved such that the tip of the needle is proximate to the end of the tube, allowing for engagement and release of the suture. As an example, FIG. 7 shows a first and second protrusion 705, 710 extending from the shaft of the needle. The protrusions may be operated by a user to push either only the tube towards to needle or to push both the tube and rod together toward the needle, thus adjusting the magnetic strength at the opening of the tube. In other words, a user may exert insertion force onto the protrusions to move the tube and/or rod. The protrusions 705, 710 are merely exemplary and the disclosure is not limited thereto, other structural components may be used to push the tube and rod toward the needle.

In yet another exemplary embodiment of the present disclosure, as shown in FIG. 6, electromagnetic coils may be used to engage and release the suture from the system. For example, an electric current may pass through the coil to generate a magnetic field. The use of an electromagnetic coil further increases the strength of the magnetic field. In particular, as shown in FIG. 6, the suturing system may include a needle 605 with a shaft 610 in which an electromagnetic coil 615 is disposed. That is, windings may be disposed along the interior of the shaft 610. Additionally, the system may include a tube 620 in which an electromagnetic coil 625 is disposed. This embodiment eliminates the need of a rod within the tube. In other words, the rod in the previous exemplary embodiment may be replaced with the electromagnetic coil 625.

Alternatively, the suturing system may include power electronics that provide current to the windings of the electromagnet from a power supply via wires, to induce a magnetic field. Power electronics and/or power supply may be housed within the shaft portion. For example, the power supply may include one or more batteries that allow the system to be fully portable. In another example, the power supply may be external to the system. The power electronics operate to control the flow of current to the electromagnet in one or more directions. For example, the power electronics may have two or three modes of operation. In a dual mode configuration, power electronics may induce an attractive magnetic field when active (e.g., attracting the suture tip) and remove the magnetic field when deactivated. In a tri-mode configuration, power electronics may induce an attractive magnetic field, induce a repulsive magnetic field by reversing the polarity of the electromagnet, or remove the current to the electromagnet completely to deactivate the magnetic field. The release and engagement of the suture in this embodiment is the same as previously discussed and thus, a further description thereof will be omitted.

Moreover, the suturing system according to an exemplary embodiment of the present disclosure may be mounted on an interface. In particular, as shown in FIG. 8, the shaft of the needle and the tube and rod combination may all be mounted to a same interface. This type of mount allows for a user to grasp the interface and operate the system with single-handle use. As shown in FIG. 8, the user may grasp the interface while still being capable of operating or pushing the tube and rod toward or away from the needle with the same hand, thus providing the user with a free hand. For example, after the needle 115 is withdrawn from a material 805 with the suture attached thereto, the user may push both the tube 105 and rod 110 together toward the needle to engage the suture with the tube 105. The engagement and release, that is, the autotransfer of the suture between the tube and the needle may be repeated until the suturing process is complete.

Figure 9A:
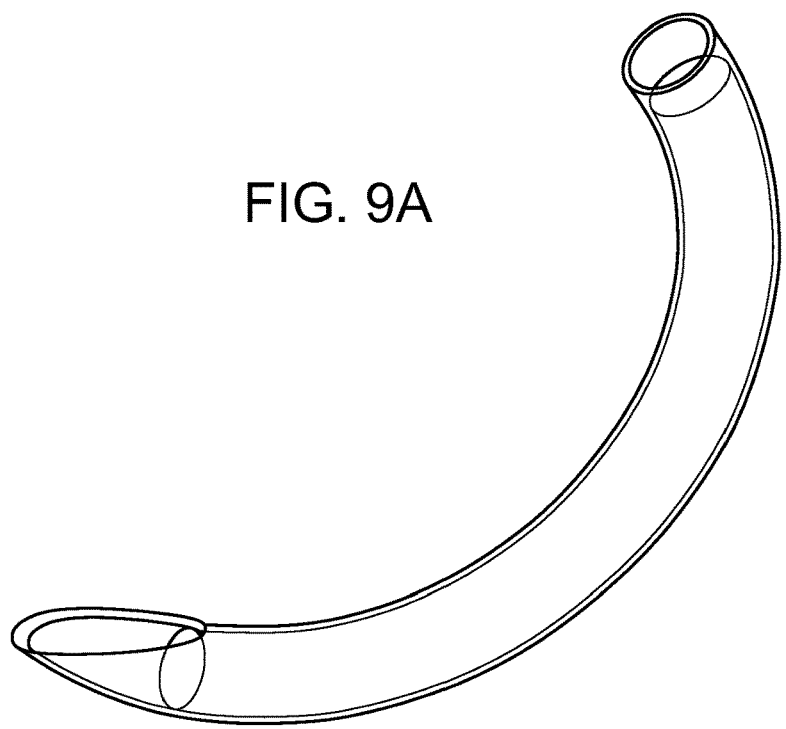
Figure 9B:
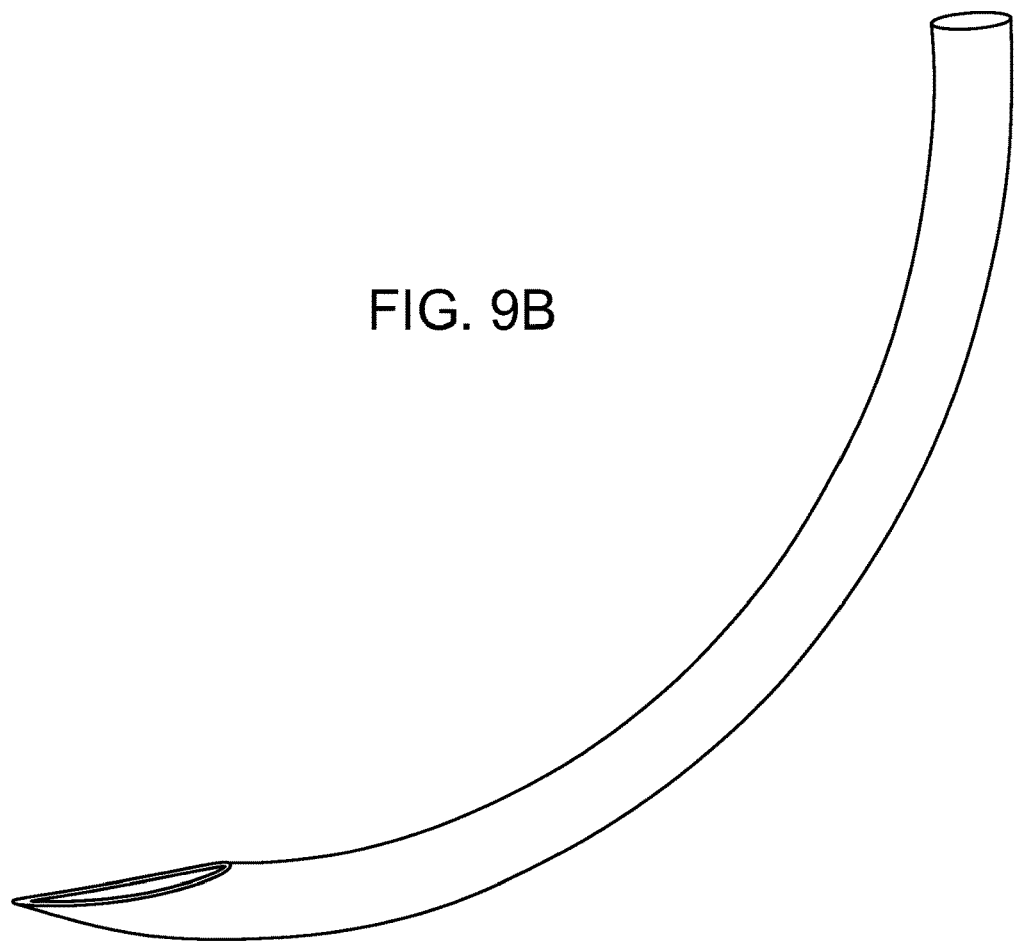
Figure 9C:
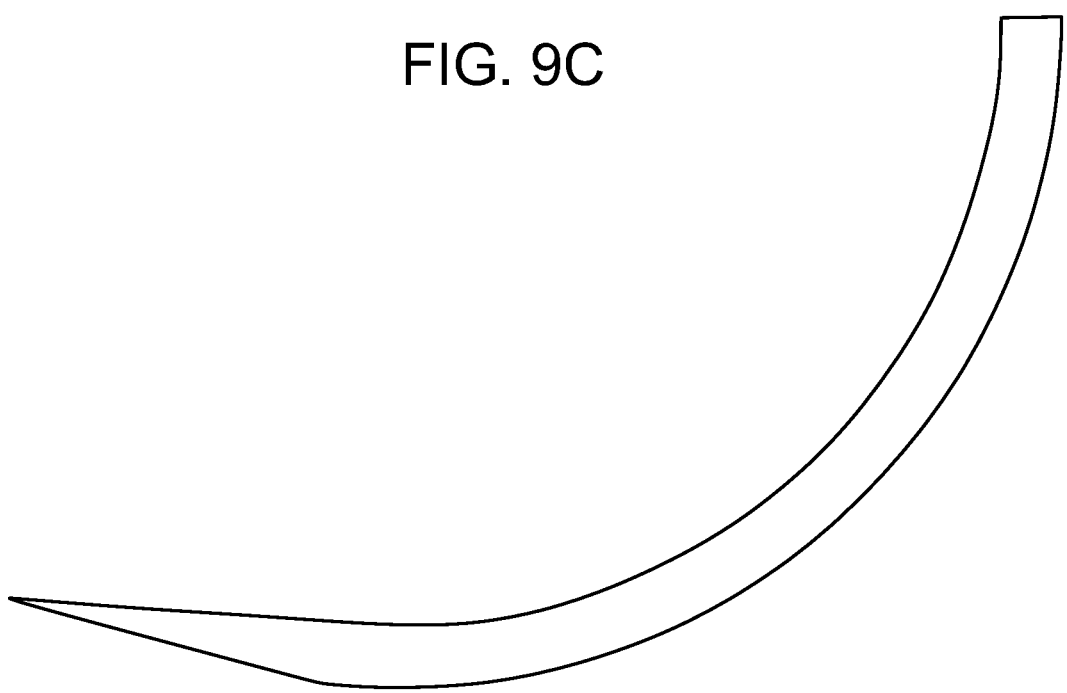
Figure 9D:
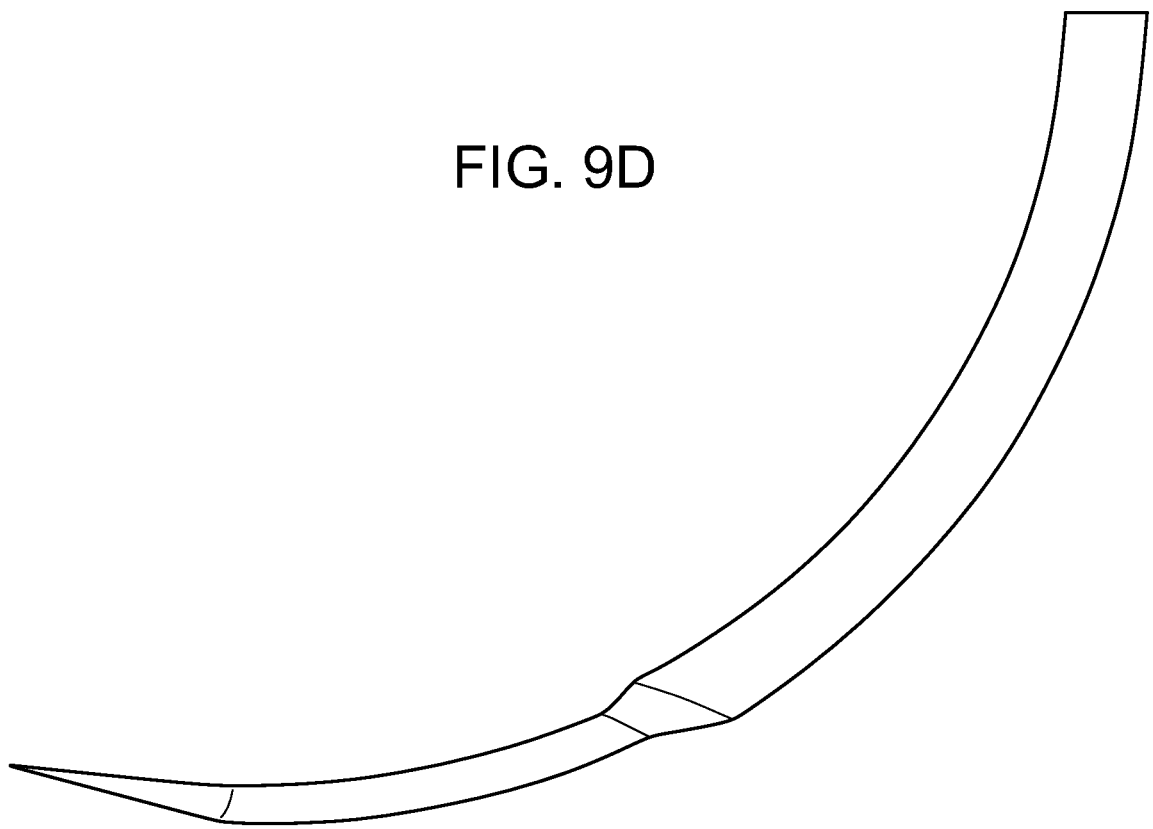

Furthermore, the tip of the needle may be formed in various shapes as shown in FIGS. 9A-9E. For example, the tip may have a front hollow space as shown in FIG. 9A to retain and secure the suture when withdrawn from a material; a flat tip as shown in FIG. 9B; a tapered tip as shown in FIG. 9C; or an elongated tapered tip as shown in FIG. 9D. Alternatively, as shown in FIG. 9E, the needle tip 905 may be tapered and an indent 910 may be formed at the end of the tip to accommodate an end of the suture, thus providing for a slimmer needle shaft 915. The present disclosure is however, not limited to the above-described needle tip shapes.

Figure 10A:
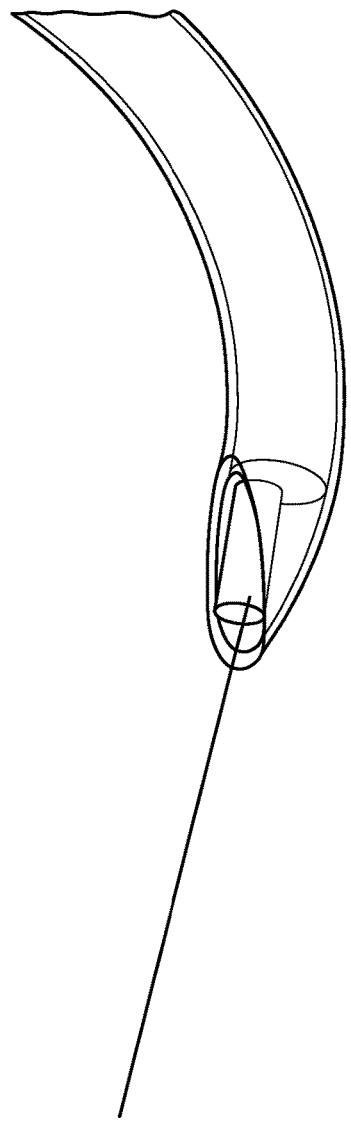
FIGS. 10A-10D illustrate various engagements of the suture and the needle of the suturing system according to an exemplary embodiment of the present disclosure.
Figure 10B:
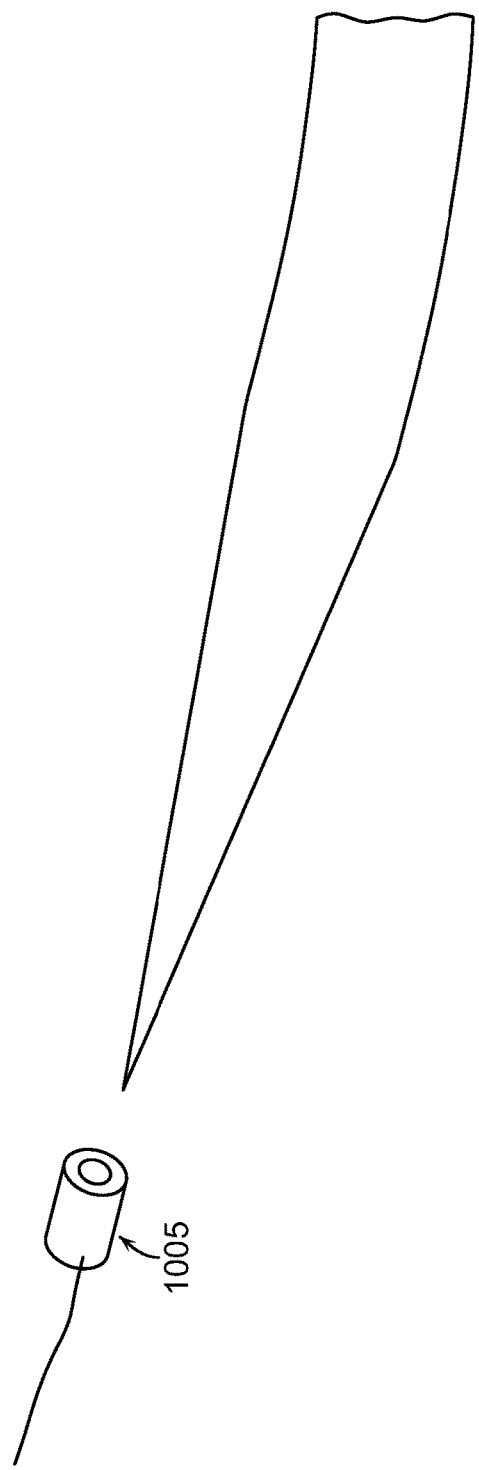
Figure 10C:
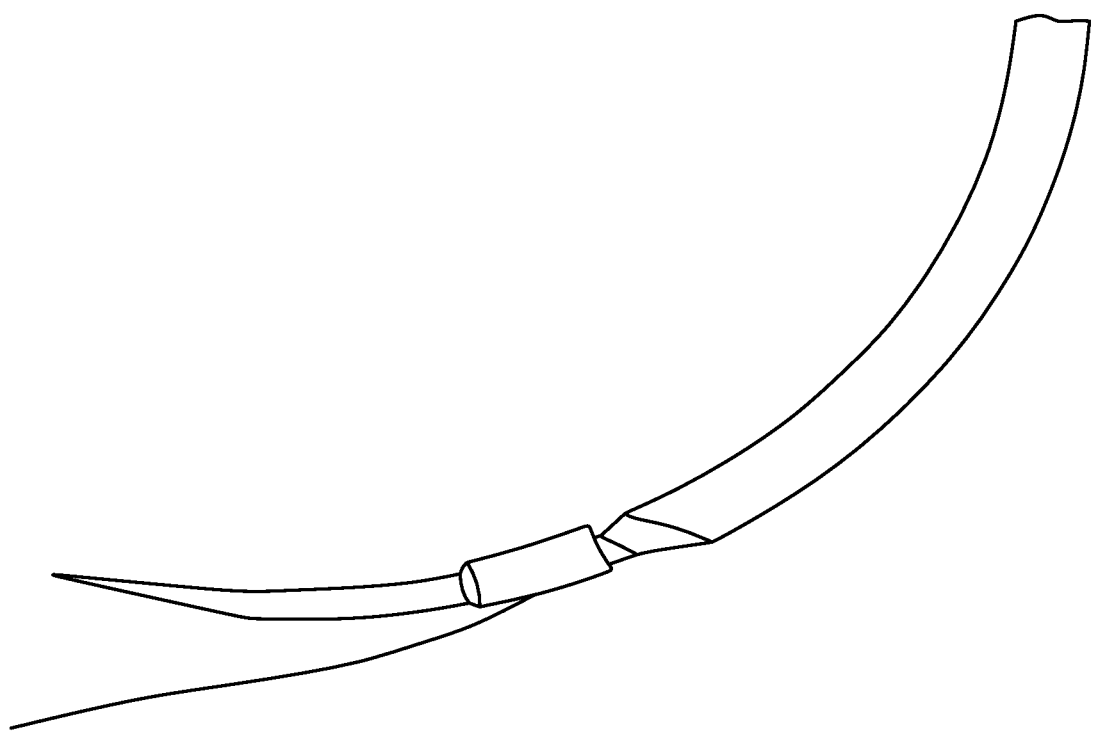
Figure 10D:
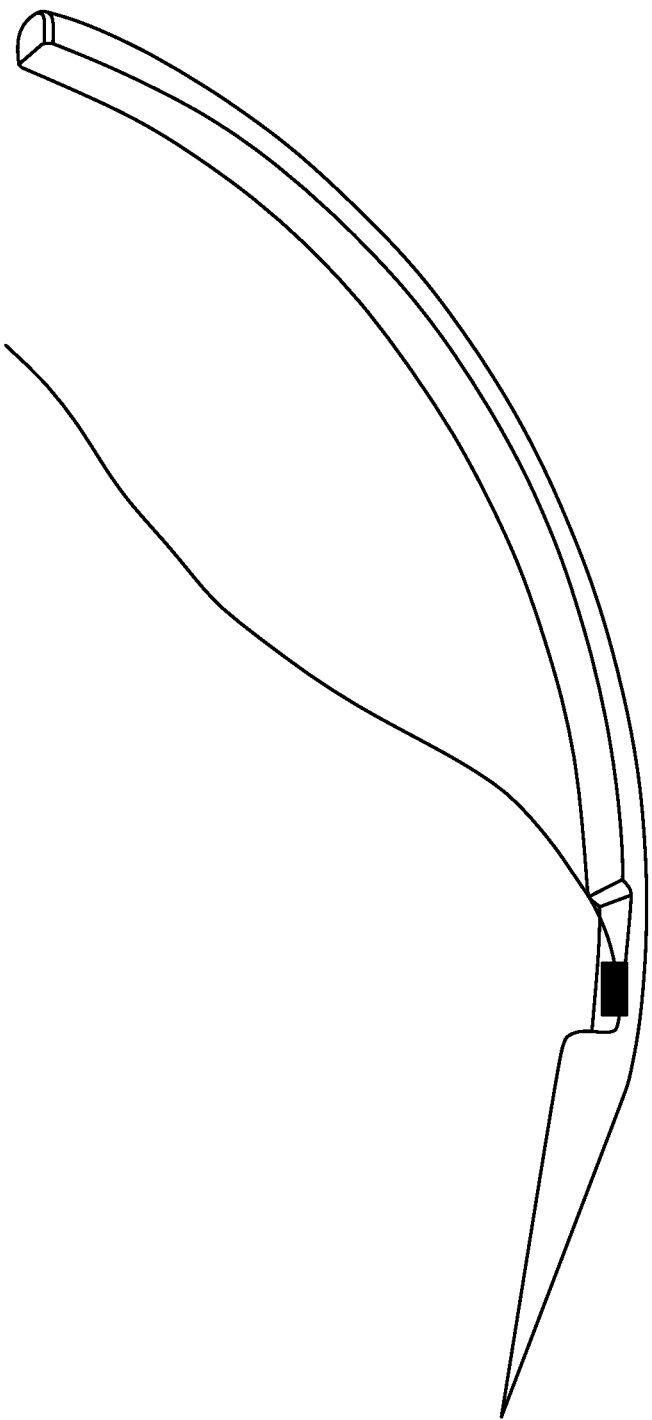

Additionally, based on the above-described variations of needle tips, the engagement connection between the suture tip and the needle may also vary as shown in FIGS. 10A-10D. First, FIG. 10A shows a connection corresponding to FIG. 9A in which the suture tip may enter into the tip of a hollow end of the needle to engage therewith. The connection shown in FIG. 10B corresponds to the needle tip shape shown in FIG. 9C. In particular, the suture tip 1005 may be ring shaped to thus slide onto the tapered tip of the needle. Similarly, FIG. 10C corresponds to the needle tip shape shown in FIG. 9D wherein a ring-shaped suture tip may slide onto the elongated taper to connect and engage with the needle. The ring-shape of the suture tip allows the suture tip to be connected to the needle to move in backward and forward directions to create the suture stitches. Lastly, FIG. 10D shows a connection that corresponds to the needle shape of FIG. 9E. As shown in FIG. 10D, the suture tip may engage with the indent 910 formed on the needle shaft.

In another aspect, the present disclosure provides a suturing method that may include engaging a suture with a tube and a magnetic rod movable within the tube and then piercing a needle through a material (e.g., tissue layers). Further, the tube may be pushed toward the needle to release the suture therefrom and engage the suture with a magnetic tip of the needle. The needle may then be withdrawn with the suture through the material. The method may further include pushing the tube and the magnetic rod together toward the needle to reengage the suture with the tube having the magnetic rod there within. The magnetic strength of the magnetic rod may be stronger than a magnetic strength of the needle tip, thus causing the suture having a magnetic tip to release from the needle tip and engage with the tube (e.g. autotransfer) when the tube and rod are pushed together toward the needle. The reengagement and release process may be repeated to complete the suturing process.

In yet another aspect, the present disclosure provides a suturing method that may include engaging a suture with a tube and a rod movable within the tube and piercing a needle through a material. The tube may then be pushed toward the needle to release the suture therefrom and engage the suture with a tip of the needle. The needle may be withdrawn with the suture through the material to begin binding the material layers together. The method may further include pushing the tube and the rod together toward the needle to reengage the suture with the tube having the rod there within. In an exemplary embodiment, the suture may be magnetically engaged with the tube and the rod or the needle and a magnetic strength of the rod may be greater than that of the needle.

The suturing apparatus according to the present disclosure provides numerous advantages. For instance, as discussed herein, the time required to perform suturing may be decreased based on the simplified system and the ability to operate the system with one hand. Since the system eliminates the need for working with two separate instruments in both hands, the system is capable of more easily suturing in traditionally less accessible locations while also providing for more accurate suturing. Additionally, since the entire needle is not required to be pulled through a material, the risk of inadvertently puncturing neighboring tissue is substantially decreased.

The many features and advantages of the disclosure are apparent from the detailed specification, and thus, it is intended by the appended claims to cover all such features and advantages of the invention which fall within the true spirit and scope of the disclosure. Further, since numerous modifications and variations will readily occur to those skilled in the art, it is not desired to limit the invention to the exact construction and operation illustrated and described, and accordingly, al suitable modifications and equivalents may be resorted to, falling within the scope of the disclosure.

What is claimed is:

1. A suturing system, comprising:
    a tube having a rod movable there within; and
    a needle having an insertion portion,
    wherein a suture engages with a tip of the needle or the tube, and
    wherein the insertion portion of the needle is inserted through a material prior to engagement with the suture, and
    wherein the tube is disposed within a hollow shaft of the needle.

2. The suturing system of claim 1, wherein the suture is magnetically engaged with the tube and the rod or the needle tip.

3. The suturing system of claim 2, wherein the tip of the needle is magnetic and the rod within the tube is magnetic.

4. The suturing system of claim 3, wherein a magnetic strength of the rod is greater than a magnetic strength of the needle tip.

5. The suturing system of claim 1, wherein the tube is pushed toward the needle to release the suture from the tube and allow suture engagement with the needle.

6. The suturing system of claim 5, wherein the tube and the rod are pushed together toward the needle to release the suture from the needle and engage the suture with the tube.

7. There suturing system of claim 4, wherein a magnetic strength of the tube decreases as the rod is retracted into the tube and the magnetic strength of the needle tip becomes greater than the magnetic strength of the tube based on the retraction.

8. The suturing system of claim 1, wherein the tube and the needle are mounted to allow single-hand use of the system.

9. The suturing system of claim 1, wherein the needle is curved such that the tip of the needle is proximate to an end of the tube.

10. The suturing system of claim 1, wherein the needle includes a hollow bevel into which the suture is engaged.

11. The suturing system of claim 2, wherein an end of the suture is magnetic to engage with the tube having the rod there within or the needle tip.

12. The suturing system of claim 11, wherein the end of the suture is ring shaped to connect with the tip of the needle upon engagement.

13. The suturing system of claim 1, wherein suture engagement is based on electromagnetic coils formed within the needle and the tube.

14. A suturing method, comprising:
    engaging a suture with a tube and a magnetic rod movable within the tube;
    piercing a needle through a material;
    pushing the tube toward the needle to release the suture therefrom and engage the suture with a magnetic tip of the needle; and
    withdrawing the needle with the suture through the material.

15. The method of claim 14, further comprising:
    pushing the tube and the magnetic rod together toward the needle to reengage the suture with the tube,
    wherein a magnetic strength of the magnetic rod is stronger than a magnetic strength of the needle tip.

16. The method of claim 15, wherein an end of the suture is magnetic.

17. A suturing method, comprising:
    engaging a suture with a tube and a rod movable within the tube;
    piercing a needle through a material;
    pushing the tube toward the needle to release the suture therefrom and engage the suture with a tip of the needle; and
    withdrawing the needle with the suture through the material.

18. The method of claim 17, further comprising:
    pushing the tube and the rod together toward the needle to reengage the suture with the tube.

19. The method of claim 18, wherein the suture is magnetically engaged with the tube and rod or the needle and a magnetic strength of the rod is greater than a magnetic strength of the needle.

* * * * *